United States Patent [19]

Adair

[11] Patent Number: 4,782,819
[45] Date of Patent: Nov. 8, 1988

[54] OPTICAL CATHETER

[76] Inventor: Edwin L. Adair, 2800 S. University Blvd., #97, Denver, Colo. 80210

[21] Appl. No.: 36,553

[22] Filed: Apr. 9, 1987

Related U.S. Application Data

[63] Continuation-in-part of Ser. No. 18,630, Feb. 27, 1987, Pat. No. 4,736,733.

[51] Int. Cl.$^4$ .............................................. A61B 1/06
[52] U.S. Cl. ...................................... 128/6; 604/264; 604/280; 604/283
[58] Field of Search .......................... 128/4, 5, 6, 7, 8; 604/264, 280, 283

[56] References Cited

U.S. PATENT DOCUMENTS

| | | | |
|---|---|---|---|
| 3,831,017 | 8/1974 | Auer | 128/6 X |
| 3,858,577 | 1/1975 | Bass et al. | 128/8 |
| 4,011,403 | 3/1977 | Epstein et al. | 358/209 |
| 4,254,762 | 3/1981 | Yoon | 128/4 |
| 4,269,192 | 5/1981 | Matsuo | 128/6 X |
| 4,313,431 | 2/1982 | Frank | 128/7 |
| 4,589,404 | 5/1986 | Barath et al. | 128/6 |
| 4,624,243 | 11/1986 | Lowery et al. | 128/6 |
| 4,736,733 | 2/1987 | Adair | 128/6 |

OTHER PUBLICATIONS

Microvasive Visicath advertisement submitted Apr. 9, 1987.

Primary Examiner—William H. Grieb
Attorney, Agent, or Firm—Fields, Lewis, Pittenger & Rost

[57] ABSTRACT

A sterilizable catheter of small diameter has a central coherent fiber bundle for carrying an image to a viewing means, and the fiber bundle is surrounded by light fibers. The proximate end of the catheter is provided with a coupling means for aligning the coherent optical bundle with the optical system of the viewing means and for providing an interface with light transmitting means to transmit light from a light source along the light fibers to the body cavity. The coupling means may have a diameter no bigger than the diameter of the covering of the catheter. When the catheter is used inside a larger endoscope or a trochar, the endoscope or trochar can be removed while the catheter remains in place. This is accomplished by removing the viewing means and sliding the endoscope or trochar over the catheter and then replacing the viewing means for further viewing within the body cavity. This device can be used for detection for cancer cells and treatment thereof by phototherapy. A fluorescent dye is attached to the cancer cells and subsequently exposed to an exciting laser light frequency. The fluorescent light is transmitted and displayed on the video monitor and the same light frequency is then transmitted through the light fibers to the cell for phototherapy treatment.

13 Claims, 7 Drawing Sheets

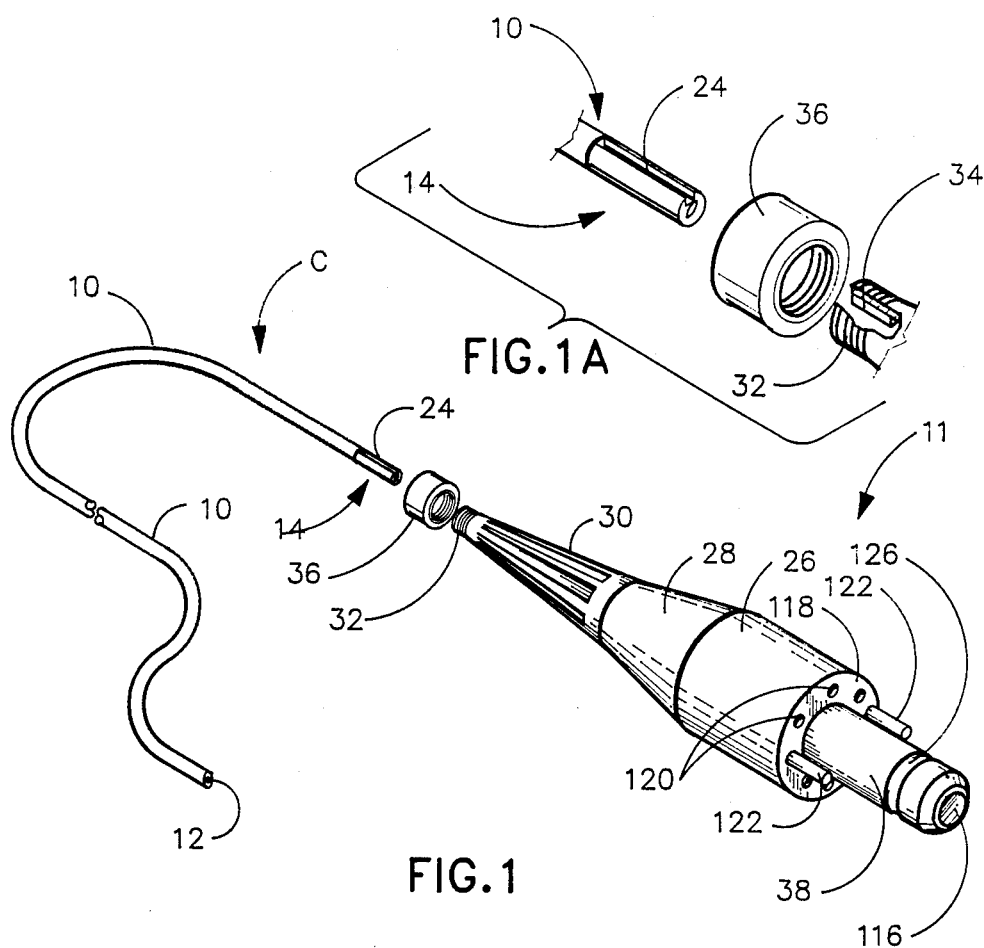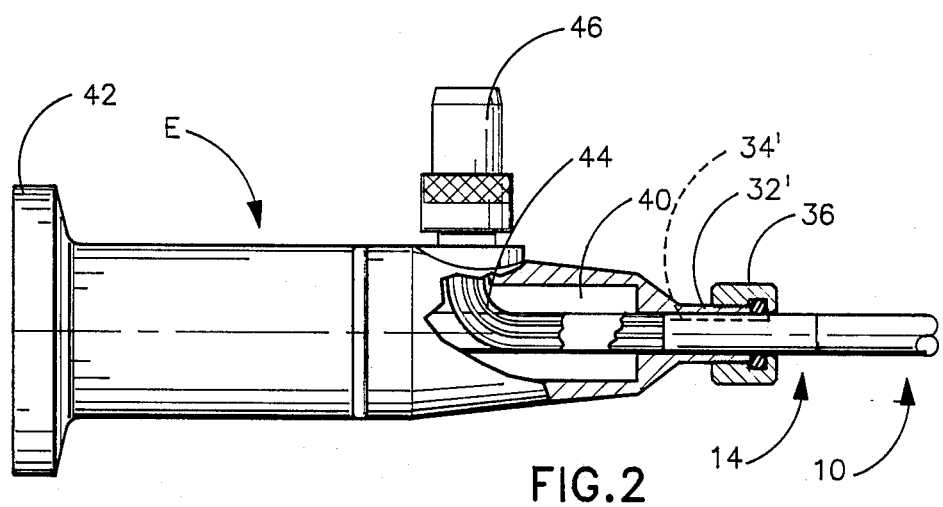

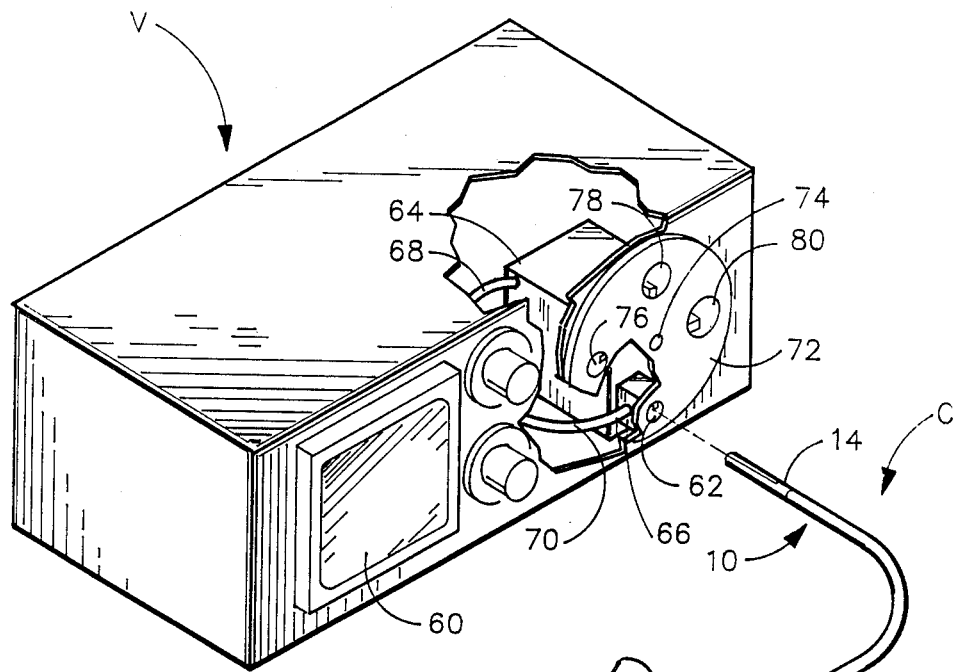
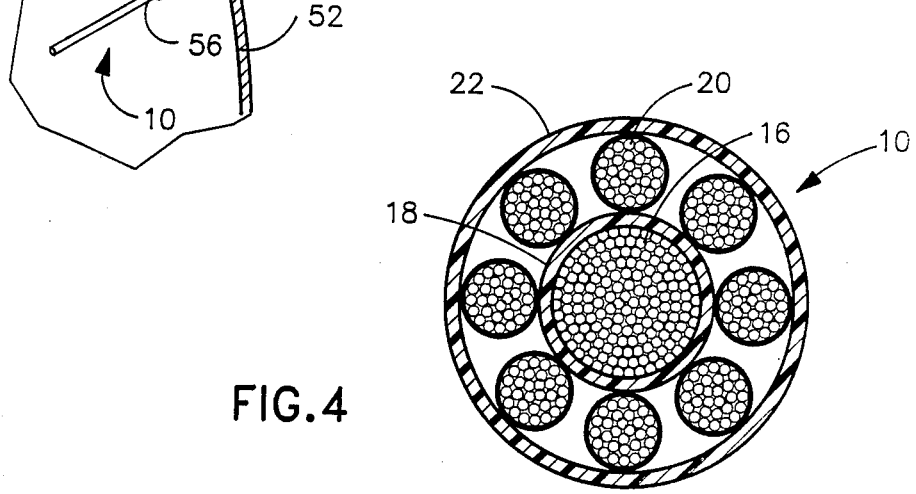
FIG. 3
FIG. 4

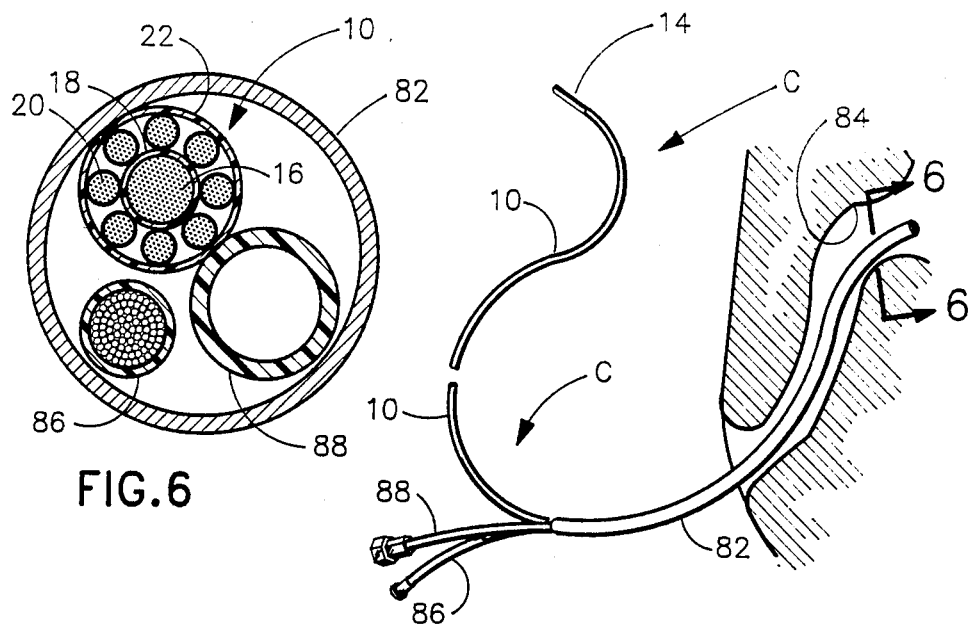
FIG.6
FIG.5
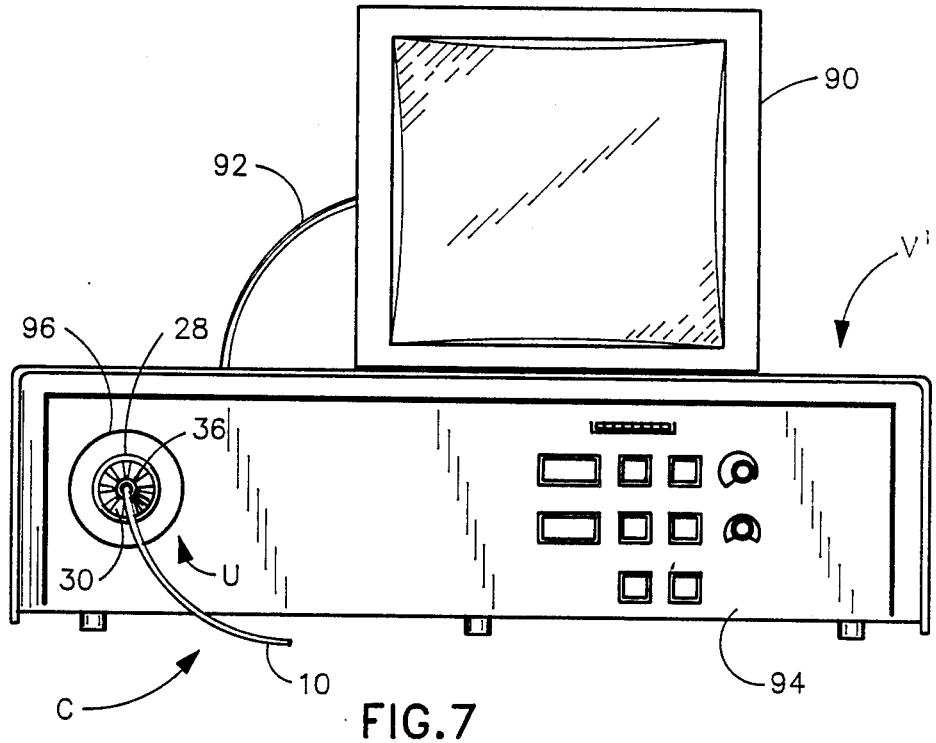
FIG.7

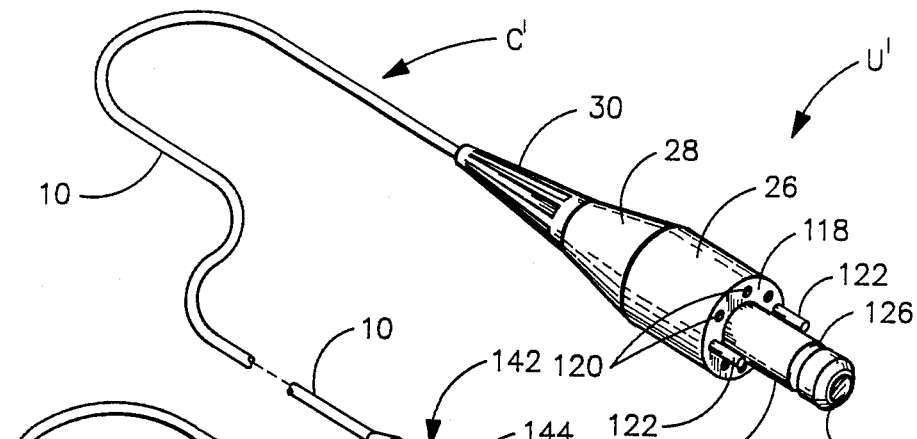
FIG. 12
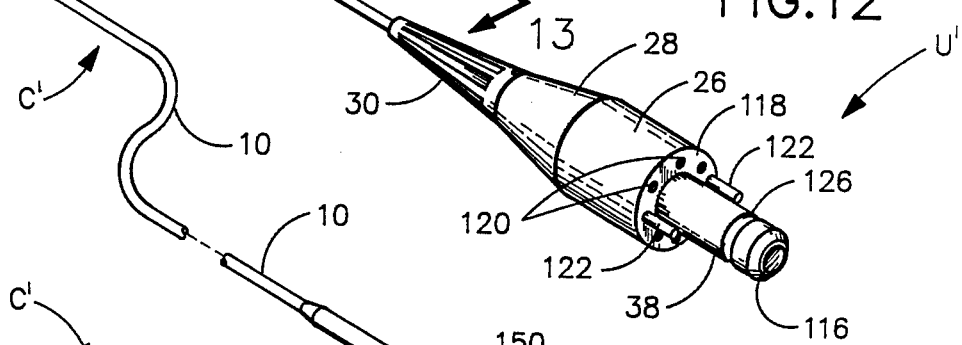
FIG. 14
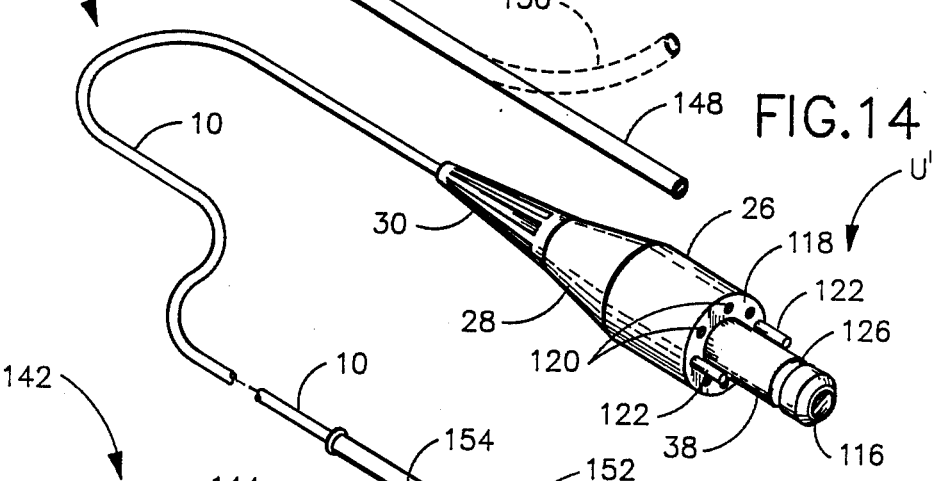
FIG. 15
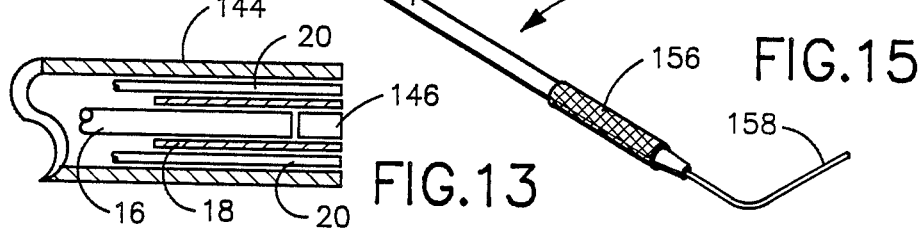
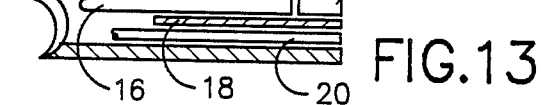
FIG. 13

OPTICAL CATHETER

This is a continuation-in-part of application Ser. No. 07/018,30 filed Feb. 27, 1987, now U.S. Pat. No. 4,736,733, granted Apr. 12, 1988.

TECHNICAL FIELD

This invention relates to small diameter endoscopes and more particularly to such an optical catheter having a coupling means on the proximate end for releasable attachment to a console for viewing by the surgeon on a video screen or monitor. In an emergency, the optical catheter may be attached to an eyepiece.

BACKGROUND ART

Prior to this invention, light beams have been used both for illumination and for treatment of disease in patients. However, all of these instruments have had eyepieces when utilized with visible light.

U.S. Pat. No. 3,858,577 to Bass, et al. discloses an endoscope of substantial size for performing laser surgery. In this device, a conventional light is used through fiber optics to illuminate the operating site and laser light is used to perform a surgical procedure.

U.S. Pat. No. 4,011,403 to Epstein, et al. discloses a fiber optic laser endoscope. The device utilizes a laser beam as a light source and an optical fiber as a light transmitter. The sensing means includes a TV camera located at the investigated site. The laser beam produces three different wavelengths which produce white light. Also ultraviolet or infrared light can be used. The camera is separate from the fiber optics and the laser.

U.S. Pat. No. 4,313,431 to Frank discloses an endoscope deploying a laser light source with a light conducting fiber. This device is used for irradiating bladder tumors utilizing the laser light beam.

Many of the problems identified above have been overcome by the invention set forth in commonly assigned U.S. Pat. No. 4,589,404 to Barath, et al. wherein an optical catheter, having a micro-thin diameter, is provided having an interface connector at the proximate end thereof for removably plugging into a receptacle in a video monitor. Thus, the catheter can be separately sterilized and can be easily replaced, should it become damaged. However, if a power interruption should occur or a malfunction cause the monitor not to work properly, the catheter disclosed in that patent can no longer be used to complete the operation. This neccesitates removal and replacement of the catheter with another one having an integral eyepiece for viewing the body cavity. This requires extra time and inconvenience and is not desirable from the standpoint of the surgeon or the patient. It also produces only a black and white image.

Another device which is currently available is an imaging lavage catheter sold under the trademark VISI-CATH ™ by Microvasive of Milford, Mass. This device has an eyepiece with a separable catheter so that the catheter can be replaced, should it become damaged. This results in a cost savings since the eyepiece does not have to be replaced. Both the eyepiece and the catheter are sterilizable. Thus, the eyepiece is not usable with a console. Thus, in the use of this device the sterility is destroyed as soon as the physician puts the eyepiece against his face.

The eyepiece requires an optical light cable to transmit light from a light source to the endoscope. Each manufacturer of optical light cables supplies them with different sized fittings at each end. This results in confusion and frustration in the operating in trying to find an optical light cable whose fittings match with those of the light source and the eyepiece.

DISCLOSURE OF THE INVENTION

This invention relates to a sterilizable optical catheter for viewing and providing treatment within body cavities by nonsurgical or micro-surgical procedures. The catheter includes a coherent fiber optical bundle of small diameter which extends from a distal end to a point adjacent to the proximate end and has a planar surface at the distal end. In addition, a plurality of light transmitting fibers are spaced around the outer surface of the optical bundle. A tubular outer cover extends over the fibers to hold them in place and the outer cover extends from the distal end to a point spaced from the proximate end. Optical lens means is provided at the distal end of the optical bundle to focus an image of a portion of the cavity on the distal end of the optical bundle for transmission through the optical bundle. A coupling means is also provided for removably connecting the catheter to a viewing means in fixed angular relationship. In a preferred embodiment the coupling means includes an integral strain relief unit which is connectable to a console unit and aligns the image bundle and light fibers therewith. It is formed as one piece with the catheter. In a secondary embodiment, the coupling means is attached to the proximate end of the catheter and has a diameter no larger than the diameter of the outer cover so that the catheter can pass completely through a trochar lumen.

More particularly, the optical catheter has alignment means to angularly align the optical bundle with the viewing means in the form of a longitudinal groove extending along the coupling means for alignment with a longitudinal rib in the viewing means. The viewing means can include a removable eyepiece having a socket for slidably receiving the coupling means in aligned relationship for viewing and alternatively can include a console containing optics and a viewing screen having a socket for slidably receiving the coupling means when not on the eyepiece, for viewing the body cavity on the viewing screen. Conveniently, the console can also include a rotatable member having a plurality of sockets spaced therearound, each socket being of different diameter for accommodating catheters constructed in accordance with this invention which also have different diameters, wherein the rotatable member is selectively alignable with the optics of the console.

From the foregoing it can be seen that a novel method of using a sterilized catheter for viewing and/or treatment within body cavities is provided which includes inserting the distal end of the catheter into a body cavity, attaching a first removable optic means to the coupling means to view the body cavity, disconnecting the first removable optic means from the coupling means, and attaching a second removable optic means to the coupling means to view the body cavity.

In addition, since the optical means is removable, the catheter can be inserted through the lumen of a larger endoscope or a trochar which has been introduced into a body cavity, the optic means being attached to the coupling means for viewing. After viewing, the optic means can be disconnected and the endoscope or the trochar can be removed over the coupling means of the catheter and the optic means reattached for further viewing, as required.

So that the optical catheter can be used interchangeably either with a console or an eyepiece, a strain relief unit is provided which has a smaller end with a socket for slidably receiving the coupling means in aligned relationship and has a second larger end with a male connector for reception in optical alignment in a receptacle of a viewing means. This viewing means can be either a console or an eyepiece. The strain relief unit can further include a bundle of optical fibers extending longitudinally therethrough to each end with are alignable with light fibers in the catheter. Alignment pins are provided adjacent the male connector to align the bundle of optical fibers in the unit with the viewing means. The body portion of the strain relief unit has a greater diameter than the male connector and forms a planar radial face at the junction between the body and the connector, the light transmitting fibers being spaced around the optic fibers and each light transmitting fiber terminating at a polished end at spaced points around the face for alignment with similar light fibers in the viewing means.

The distal end of the catheter may take a number of forms for different usages. For example, if it is used as an arthroscope a rigid metal jacket may be required around the ends so that it can be introduced through an opening formed in the joint to be examined. In some applications it might be desirable to have the rigid sleeve made of maleable material, such as sterling silver so that the device can be bent to fit the needs of the surgeon in viewing a particular part of a joint. Also, if the device is used as a hysteroscope a maleable sheath will allow the surgeon to mold it to fit the uterine cavity of each patient. It could also be attached by means of a protective metal tube to a pair of forceps for extracting fish bones or other lodged or foreign objects from the larynx, by way of example.

In addition, if a special light source, special optical filters and special light conducting fibers are built into the optical catheter, it can be used for the detection and treatment of abnormal cells, such as cancer cells. In this regard the patient is given a drug which has a particular affinity to the abnormal cells and which will fluoresce when exposed to light of a predetermined first frequency. This light frequency can be transmitted through special light fibers of the optical catheter onto the tissue being examined. When florescence is viewed on the monitor or with the eyepiece, the surgeon will know that this is a site of abnormal cells. Light of a second frequency which will kill the cells can be directed down the light fibers or through a separate and additional light fiber. If still a third light channel is provided, to permit the use of other light frequencies, various quantative measurements can be done through the revised catheter. In some situations, strobed light may be used.

Additional advantages of this invention will become apparent, when taken in conjunction with the accompanying drawings.

BRIEF DESCRIPTION OF THE DRAWINGS

FIG. 1 is a perspective view of one form of an optical catheter constructed in accordance with this invention showing specific details of the coupling means and the eyepiece;

FIG. 2 is a fragmentary side elevation of one configuration of an eyepiece showing the interconnection of the catheter and the optics within the eyepiece;

FIG. 3 is a perspective view showing the use of the optical catheter of this invention with a trochar which is inserted into a body cavity and is used with a console;

FIG. 4 is an enlarged cross section of the distal end of the optical catheter constructed in accordance with this invention.

FIG. 5 is a perspective view of the optical catheter of this invention used with a maleable sheath in a multilumen trochar;

FIG. 6 is an enlarged cross section, taken along line 6—6 of FIG. 5, showing the end of the optical catheter of this invention, when used in a multilumen trochar;

FIG. 7 is a front elevation of a console and video monitor connected to an optical catheter of this invention;

FIG. 12 is a perspective view of a preferred form of the optical catheter of this invention with a general purpose rigid examining tip on the distal end;

FIG. 13 is an enlarged longitudinal section, taken along 13—13 of FIG. 12, showing details of the end construction;

FIG. 14 is a perspective view of the optical catheter of this invention, which is similar to FIG. 12, but shows a stainless steel sheath on the distal end which may be either rigid or maleable;

FIG. 15 is a perspective view of the optical catheter of this invention, similar to FIGS. 12 and 14, but showing an optical probe at the distal end of the catheter.

BEST MODE FOR CARRYING OUT THE INVENTION

Figure 8:
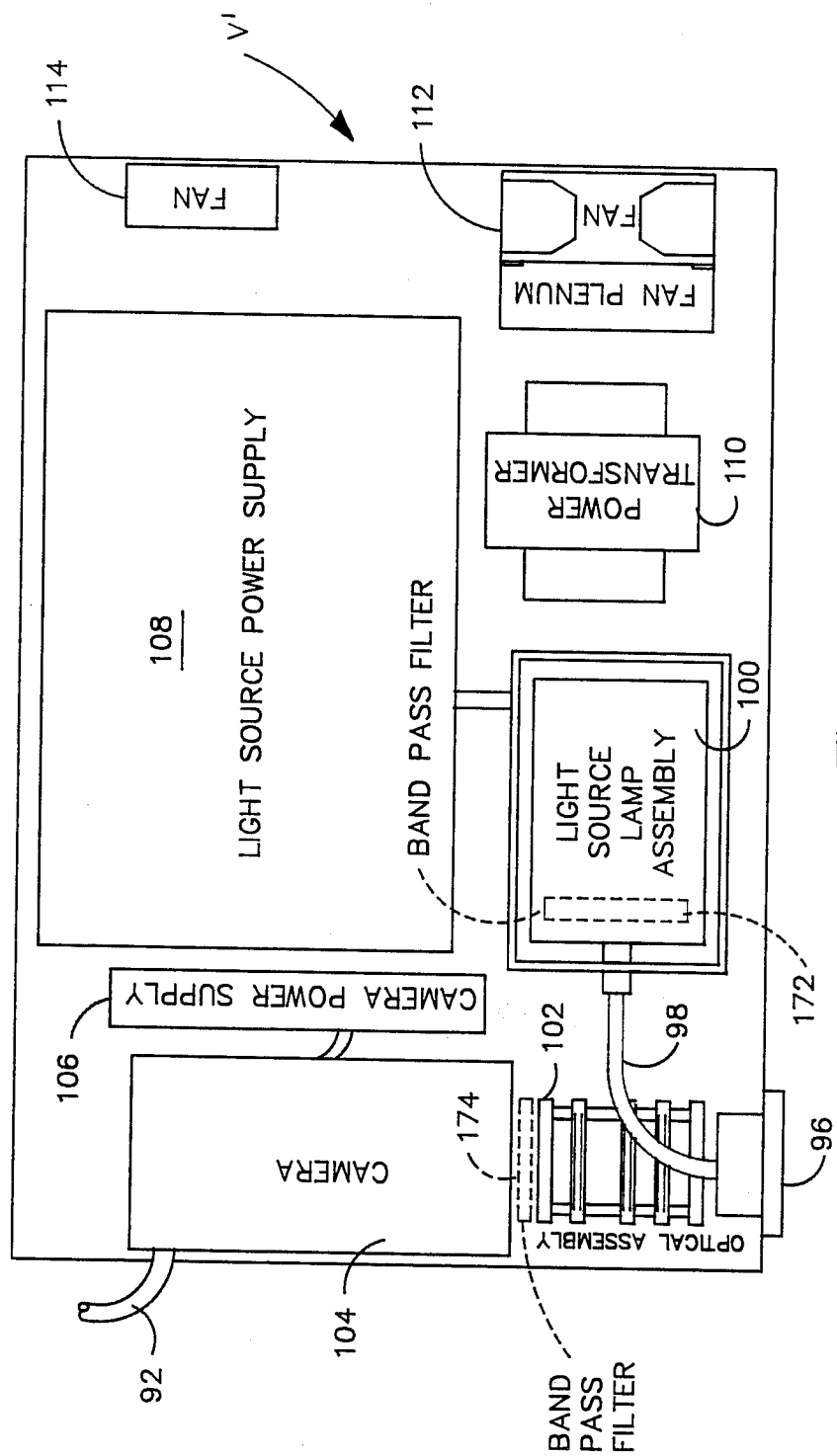
FIG. 8 is a diagrammatical plan view of the interior construction of the console of FIG. 7.

In accordance with this invention, one form of a sterilizable small diameter optical catheter C is provided as shown in FIG. 1. This catheter includes a cable assembly 10 which is provided a its distal end with a lens 12 and at its proximate end with a coupling means 14. Turning to FIG. 4, an enlarged cross section of cable assembly 10 is shown. At the center of the cable is a coherent fiber optical bundle 16, a tubular inner cover 18 extends around coherent optical bundle 16 at each end and may be formed of a heat shrinkable Teflon or PVC material which extends along the coherent optical bundle from the distal end to the proximate end. Placed around inner covering 18 are a plurality of light carrying bundles 20 which are made up of individual fibers which do not have to be coherent. These bundles are for transmitting light from a suitable light source to the body cavity. Alternatively, bundle 20 may be replaced with a single flexible glass fiber. An outer cover 22 extends around the spaced light bundles 20, as shown and may also be constructed of a heat shrinkable Teflon material which extends from the distal end of catheter 10 to a position adjacent coupling means 14. The coupling means 14 is located at the proximate end of outer cover 22 and includes a longitudinal groove 24 for alignment with a mating rib in a viewing means or in a strain relief unit for connection to a viewing means. It can be made of any suitable material, such as anodized aluminum or a machinable grade of plastic, such as Bakelite.

A strain relief unit U also is illustrated in FIG. 1 which can be used to connect the catheter C either to a console or to an eyepiece, as will be more fully explained below. The strain relief unit U has a cylindrical body 26 having a first tapered section 28 and a second smaller taper section 30, as shown. The second tapered section 30 terminates at its distal end in a socket 32 having a longitudinal rib 34 alignable with groove 24 and held in place by locking nut 36. The other end of strain relief unit U has a male connector 38 which is receivable in a console or an emergency use eyepiece, as will be described more fully below. By having the strain relief unit removable from catheter C, it is possible to withdraw a trochar through which the catheter may extend, also as explained below.

In addition, the catheter can be connected to a eyepiece is shown in FIG. 2 which has a coupling means identical to that of strain relief unit U so that it can be coupled to catheter C. It has a socket 32' with a longitudinal rib 34' that is alignable with the groove 24 of coupling means 14. Thus, the coupling means can be slid into the socket as best seen in FIG. 2 and held in position by threaded locking nut 36. The proximate end of coupling means 14 and the fibers are flat and polished so as to come into contiguous face-to-face contact with a rod lens 40 for transmitting the light from the coherent fiber bundle to the user's eye which is held against the ocular face 42. The alignment of groove 32' with rib 34' assures that the image being transmitted by the coherent optical bundle 16 is in proper orientation with respect to lens 40 of eyepiece E. Light fibers 44 surround lens 40 and extend to a fixture 46 to which a suitable light source can be attached for illuminating the body cavity by transmitting light along fibers 44 and light bundles 20.

Because coupling means 14 has a diameter no larger than that of outer cover 22, it can be used in a more versatile manner than heretofore possible. FIG. 3 discloses a trochar 50 which is illustrated as being inserted through the wall 52 of a body member and into a body cavity 54. The trochar has a first lumen 56 through which the catheter C extends into the body cavity 54. A second lumen 58 is provided for any one of a number of purposes, such as for irrigation or treatment within the body cavity 54. As is well known, trochars of this type may have more than two lumens, depending on their intended use.

After the procedure is completed through lumen 58, it may be desirable to remove trochar 50 while leaving catheter C in place for further viewing. With the present invention this is possible using either the eyepiece of FIG. 2 or the video console of FIG. 3.

If an eyepiece E is used, as shown in FIG. 2 is used, it can be removed by removing locking nut 36 and sliding the coupling means 14 of the catheter out of socket 32'. Since the coupling means 14 is no bigger in diameter than outer cover 22, the trochar can be slid to the right, as viewed in FIG. 3, while leaving catheter C in place. After removal of trochar 50, the eyepiece E can be reconnected to the coupling means 14, as previously described. The surgeon can then resume his viewing of the body cavity, as required.

Conveniently, the sterilizable catheter of this invention can also be used with a video console V, of the type shown in FIG. 3. This console includes a video screen 60. The coupling means 14 of catheter C is receivable in a socket 62 which is connected to a camera 64 by suitable optics 66 which includes a continuous focus zoom lens for transmitting the image to camera 64. A light source (not shown) is provided and is connected to optics 66 by light cable 70. It is contemplated that the invention might be utilized with catheters of different diameters for different purposes. Thus, socket 62 can be provided in a disc 72 which is mounted for rotation on the video console V about an axis 74 and is provided with a plurality of other sockets, such as sockets 76, 78 and 80, as shown. The socket corresponding to the size of the catheter can be rotated to be in the position of socket 62, so as to be properly aligned with the optics 64.

An important advantage of this invention is that when a cable assembly 10 of the catheter becomes damaged and no longer usable, it can replaced with another one without having to replace a corresponding eyepiece. Furthermore, the catheter of this invention can be made to be moisture impervious so that it can be easily sterilized for reuse. When used with a console, the sterility of the operating environment can be maintained since the surgeon does not need to put an eyepiece against his face. Furthermore, when the device is used with the video monitor V, should there be a power interruption or should the video camera or monitor malfunction, it is merely necessary to slip the coupling means 14 of the catheter out of its socket, such as socket 62, and attach a sterilized eyepiece E, which would be provided to the surgeon, so that he can continue with the operation or procedure with minimal interruption.

In an alternative embodiment, shown in FIG. 5, catheter C extends through a maleable sheath 82 which extends through a body canal 84 and is conformed to the shape of the canal. In addition to catheter C, the sheath 82 may include a laser fiber 86 for phototherapy or photocoagulation treatment within the body cavity into which the sheath and catheter extend. Additionally, it may include a passageway 88 for irrigation or suction.

A video console V' is shown in FIG. 7 which is specifically constructed for use with the strain relief unit U which couples catheter C to the console. In this embodiment, a video monitor 90 is provided as a separate unit and is connected to the console by a signal transmitting cable 92. The console V' has a front panel 94 which contains the controls for the monitor camera, light source and filters, as well as a receptacle 96 for receiving strain relief unit U. As best seen in FIG. 8, the receptacle 96 is connected by means of a light cable 98 to a light source 100. The receptacle 96 also is connected to an optical assembly 102 which transmits the image from the cable to camera 104 for transmission by cable 92 to the monitor 90. The camera is connected to a camera power supply 106 and the lamp assembly is powered through light source power supply 108. A suitable power transformer 110 and fans 112 and 114 are provided.

Returning now to FIG. 1, the male connector 38 carries an optical bundle 116 through the center thereof which aligns with the optical bundle 16 in catheter C at socket 32 and is polished at both ends so that light will be transmitted from one bundle to the next. A flat face 118 radiates outwardly from connector 38 to the peripheral surface of cylindrical body 26. The ends of light transmitting fibers 120 are spaced around this face and also have polished ends, the opposite ends thereof being aligned with the ends of light bundles 20 of catheter C. Alignment pins 122 are provided on opposite side of connector 38 to align the light bundles and optical bundles with the corresponding light transmitting fibers within video console V'.

Figure 9:
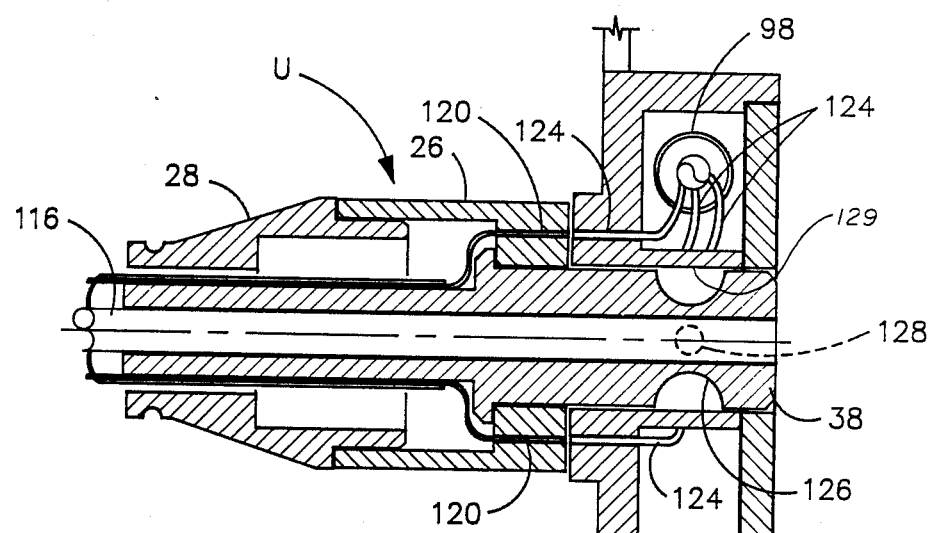
FIG. 9 is an enlarged longitudinal section through the socket of the monitor and the strain relief unit of the catheter showing the interconnection between the two.

Turning to FIG. 9, it can be seen that within receptacle 96 are spaced light bundles 124 which align with light bundles 120. These light bundles are fed through light cable 98 to light source lamp assembly 100. Thus, it can be seen that the light will be transmitted via all these light bundles from the light source lamp source assembly to the end of catheter C for illuminating the area to be viewed. The image will be transmitted through the optical bundles, as described to the optical assembly 102 and camera 104. Conveniently, connector 38 has a peripheral recess 126 for receiving a spring detent 128 in the receptacle 96 to releasably hold the strain relief unit U in place in socket 129.

Figure 10:
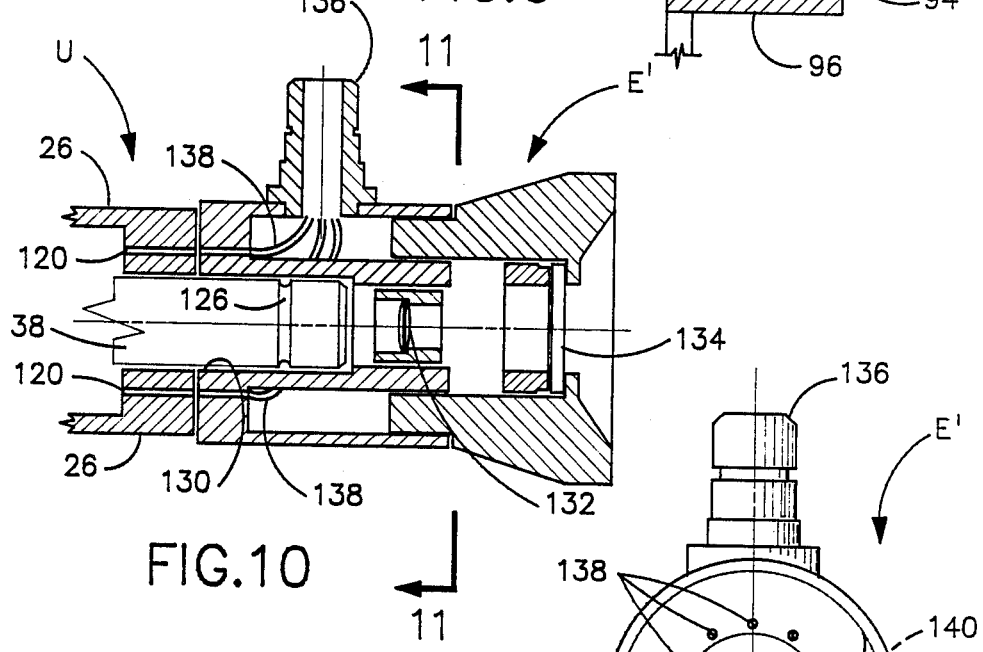
FIG. 10 is a similar section through an eyepiece showing the interconnection between the eyepiece and the strain relief portion of the catheter.
Figure 11:
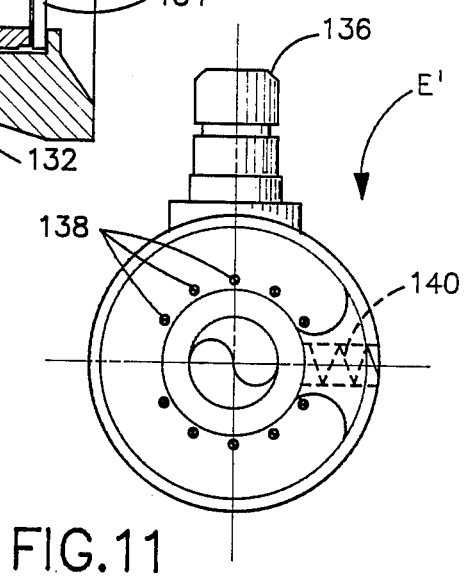
FIG. 11 is a vertical section, taken along 11—11 of FIG. 10 showing the spring detent for holding the strain relief unit in position.

An eyepiece E' as shown in FIGS. 10 and 11 which is connectable to strain relief unit U as shown. The eyepiece includes a socket or receptacle 130 in which the male connector 38 extends. The light bundle thereof is aligned with lens 132 whereby the image is projected through glass window 134 onto the eye of the surgeon. The eyepiece E' is also provided with a light fixture 136 through which a bundle of light transmitting fibers 138 extend and terminate in peripherally spaced positions around the face of the eyepiece for alignment with the light bundles 120 of strain relief unit U. As best seen in FIG. 11, a spring detent 140 extends into the peripheral groove 126 of male connector 38 to releasably hold the strain relief unit and eyepiece E' together.

An alternative, but preferred, optical catheter C' having an integral strain relief unit U' is shown in FIGS. 12-6. The length of this device is approximately 75 to 80 inches in length and is very flexible. The tapered section is cable of accepting optical catheters of different diameters in the distal end. Each optical catheter in the respective Figures has a different tip. A general purpose tip 142 is shown in FIG. 12. This tip may be the same diameter as the optical catheter or enlarged, as shown. This tip may include a stainless steel jacket 144, as best seen in FIG. 13, or it may not have a metal covering at all and be very flexible. As can be seen from this figure, within the jacket 144 is optical bundle 16 having a cover 18 and being surrounded by spaced light bundles 20. Conveniently, a lens 146 is provided at the end of optical bundle 16 for focusing an image of the site being investigated on to the end of light bundle 16 for transmission to the viewing means.

In FIG. 14 a long straight probe 148 is illustrated which may be a stainless steel jacket made of #304 tempered stainless steel. Also, #316, #316L and IN-CONEL TM 600 steel may be used. This device may be used for insertion into various body passageways which are relatively straight. Alternatively, a maleable jacket 150 (shown in dotted lines) may be used which can be conformed to the passageway through which it is to extend. Such usage of this device might be as an arthroscope and the maleable material may be sterling silver. With this device the surgeon can bend it to fit his needs to see a particular part of the joint in which it is used. After the procedure is completed, it can be straightened for use in the next succeeding case. In small joints, such as a finger joint, the device might be approximately 1.0 mm in diameter. If it is intended for use in examining an ankle joint it might be 2.0 mm in diameter. And still larger joints like a knee, it might be 3.5 mm to 5.0 mm in diameter, or possible larger. The metal sleeve can be approximately 6" to 8" in length. In the maleable device, a maleable form of stainless steel might be used instead of sterling silver. A closely wound steel spring of appropriate length may be provided to slip over the maleable section to aid the surgeon to shape this section to desired configuration without crimping. This steel spring is then removed after shaping and set aside.

If the device is used as a hysteroscope it might be made less than 1.0 mm in diameter. This size is selected to allow passage of the device into the cervical canal without dilating the cervix. If made this small, the optical catheter of this invention can be passed into the cervix along with such other devices such as a special fiber optic, possible of 200 to 400 microns diameter for transmitting laser energy for photocoagulation as previously discussed with respect to FIG. 5. Also a channel for either suction or irrigation can be provided. With the maleable sheath, the device can be preformed to the shape of the particular uterine cavity in which it is being used.

In the embodiment of FIG. 15 an optical probe 152 is illustrated which has a rigid body portion 154 with a hand grip 156 and a curved rigid probe 158 which allows the physician directional stability so that he can point the device wherever he wants it to look around other body portions.

Figure 16:
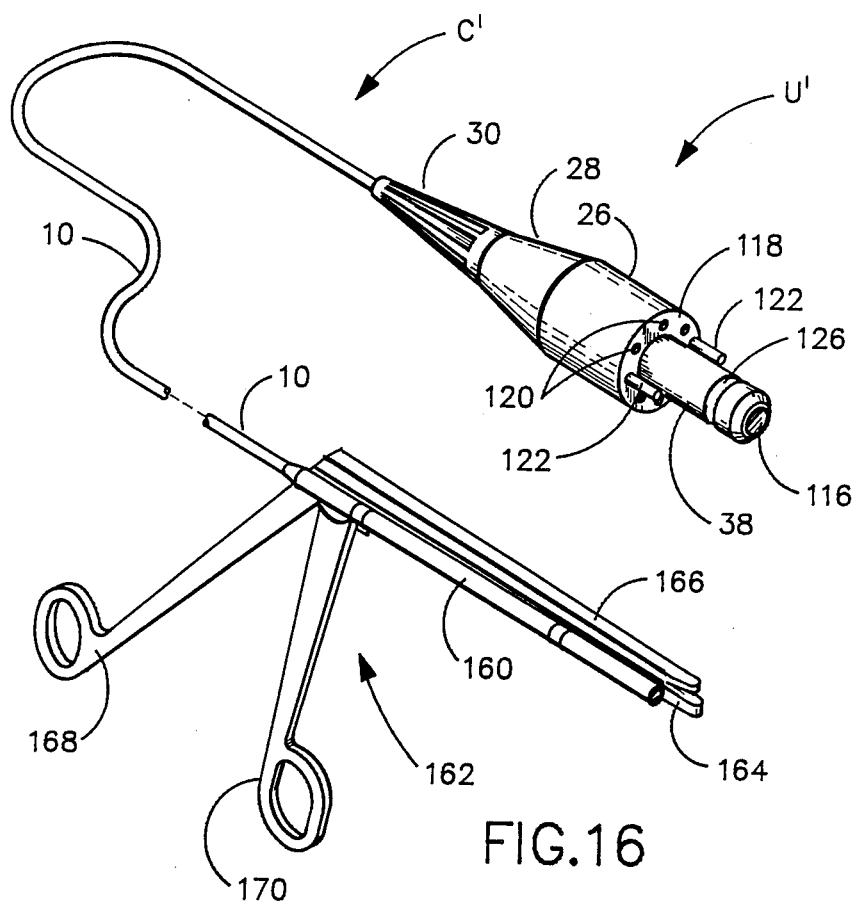
FIG. 16 is a perspective view of the optical catheter of this invention, similar to that shown in FIGS. 12, 14 and 15, but showing the distal end in a protective tube attached to grasping jaws of a pair of forceps.

A still further embodiment is shown in FIG. 16 wherein the catheter C' extends into a protective stainless steel housing 160 which is attached to the side of a pair of forceps 162, such as a laryngeal grasping device which might be used to extract a fish bone from the larynx. The metal tube is welded or otherwise attached to lower jaw 164 of the instrument. The upper jaw 166 can be moved relative to jaw 164 by squeezing handles 168 and 170 respectively. Thus, when the physician inserts the grasping device into the throat patient he can look around and determine where the lodged object is.

It will be understood that other uses will become apparent to one skilled in the art in addition to those illustrated.

With slight modification, the optical catheter of this invention and the console can be used as a fluorescence detector and provide a means for not only detecting abnormal cells but also for treating the cells by phototherapy and measuring the effectiveness of that treatment.

One drug that has been found to be ideal for detecting abnormal cells, such as cancer cells is a hematoporphyrin derivative (HPD). When exposed to a light frequency between 400 nm and 410 nm it will fluoresce to a salmon pink color having a wave length of 630 nm. If the tumor containing the drug is then exposed to an external laser frequency 630 nm the cancer cell is destroyed with no harm to surrounding normal cells. This is referred to HPD phototherapy. The cancer cells are destroyed because the 630 nm light causes a change in the oxygen in the cell to a form called "singlet oxygen" this substance is toxic to the cell. The oxygen content of the cell can be monitored by utilizing laser light to measure absorption spectra and by a spectrophotometer. Turning to FIG. 8, it will be apparent that the lamp and light source lamp assembly 100 can be changed, such as to a halogen light which provides a frequency in the visible range or alternatively a band pass filter 172 can be inserted which allows transmission of only those light rays which fall within the desired frequency. The fluorescing cells will then transmit light through the optical assembly to camera 104. Again, a second band pass filter 174 can be inserted between the optical assembly and the camera which allows transmission only of the reflective fluorescent light in the range of 630 nm. Also, various electronic equipment, known in the art for image processing and image enhancement to increase the brilliance of such an image can be utilized to make the fluorescing cells clearly visible to the physician on the video monitor 90. Furthermore, band pass filter 172 can be replaced by other filters, and can provide for allowing a different light frequency then in the range of 630 nm to be transmitted. These two frequencies of 410 nm and 630 nm can be strobed so that they are alternately sent along the light fibers for fluorescence and for killing the cells, respectively.

Although a particular photochemical material and light range has been described, it will be understood that other photochemical materials may give off other light frequencies which could be anywhere from the infrared frequency through the visible frequency to the ultraviolet frequency. In addition to a halogen light source, a mercury vapor light source or a Xenon light source could be used with the band pass filters.

In addition, the catheter can be changed to provide fibers which are particularly effective for transmitting light in the 400 nm to 410 nm frequency range. Such fibers are available through Gallileo Electro-Optics Company of Sturbridge, Massachusetts and other manufacturers. Another fluorescence detector compound which has been found effective is Rhodamine-123.

From the foregoing, the advantages of this invention are readily apparent. An optical catheter has been provided which has great versatility in that it may be used with either a substantially standard eyepiece or with a video camera and monitor. The catheters can be provided in different sizes when used with a video monitor, which may contain a plurality of sockets for alignment with the optical means of the video camera for connection with a catheter of the selected size. Furthermore, the catheter can be used within the lumen of a trochar or operating channel of a larger endoscope and since the eyepiece is removable the trochar or larger endoscope can be removed without removing the catheter and then the eyepiece can be replaced for further viewing. The catheter can easily be replaced should it become damaged, without replacement of the expensive viewing means. Also, the sterility of the catheter can be maintained when used with the console, which permits its use with a lower risk of infection. Furthermore, no separate light cable is needed.

The device can also be used for detection and treatment of cancer cells or other abnormal cells by using it to excite a fluorescent dye in the abnormal cell by excitation with a selected laser light. The fluorescence will give off its own light which can be detected and displayed on the video monitor whereupon a laser light of the same frequency can be transmitted back to the cell and used to convert the oxygen in the cell to singlet oxygen thereby destroying the cell. The effect of the phototherapy can be monitored by photometric means.

This invention has been described in detail with reference to particular embodiments thereof, but it will be understood that various other modifications can be effected within the spirit and scope of this invention.

I claim:

1. A sterilizable small diameter optical catheter for viewing and/or treatment within body cavities by non-surgical or micro-surgical procedures and having a distal end for insertion into a body cavity and a proximate end, said catheter comprising:
    a coherent fiber optical bundle having a micro-thin diameter and extending from said distal end to a point adjacent said proximate end and having a planar surface at its proximate end;
    a plurality of light transmitting fibers spaced around said optical bundle;
    a tubular outer cover extending over said fibers to hold them in place, said outer cover extending from said distal end to a point spaced from said proximate end;
    optical lens means at said distal end of said optical bundle to focus an image of a portion of the cavity on said distal end of said optical bundle for transmission through said optical bundle;
    a coupling means for removably connecting said catheter to a viewing means in fixed angular relationship, fixedly attached to said proximate end of said catheter and having a diameter no larger than the diameter of said outer covering so that said catheter can pass completely through a trochar lumen or operating channel of a larger endoscope; and
    a strain relief unit having a first smaller end for receiving said coupling means in aligned relationship and having a second larger end with a male connector for reception in optical alignment in a receptacle of a viewing means.

2. A catheter, as claimed in claim 1, wherein said strain relief unit includes:
    a bundle of optical fibers extending longitudinally therethrough to each end which are alignable with light fibers in said catheter; and
    alignment pins adjacent said male connector to align said bundle of optical fibers in said unit with the viewing means.

3. A catheter, as claimed in claim 2, wherein said strain relief unit further includes:
    a body portion having a greater diameter than said male connector and forming a planar radial face at the juncture between said body and said connector, said light transmitting fibers being spaced around said optical fibers, each light transmitting fiber terminating at a polished end at spaced points around said face for alignment with similar light fibers in the viewing means.

4. A catheter, as claimed in claim 3, further including:
    a tapered section joining said body and said smaller end.

5. A catheter, as claimed in claim 1, further including:
    a stainless steel jacket encasing the distal end of said catheter.

6. A catheter, as claimed in claim 5, wherein:
    said jacket is rigid.

7. A catheter, as claimed in claim 5, wherein:
    said jacket is maleable to assume the contour of the body canal in which said catheter is placed.

8. A catheter, as claimed in claim 5, wherein:
    said jacket is attached to a pair of forceps.

9. A catheter, as claimed in claim 5, wherein:
said jacket is in the form of an optical probe having an angular bend.

10. A catheter, as claimed in claim 1, wherein said viewing means includes:
a removable eyepiece having a socket for slidably receiving said coupling means in aligned relationship for viewing; and
a console containing optics and a viewing screen having a socket for slidably receiving said coupling means when not on said eyepiece, for viewing the body cavity on said viewing screen.

11. A catheter, as claimed in claim 10, wherein: said console includes:
an optical assembly including said receptacle;
a light source;
a receptacle;
light fibers for transmitting light from said light source to points spaced around said receptacle;
a camera aligned with said optical assembly for receiving images from the optical bundle of said catheter; and
a video monitor connected to said camera for displaying the images.

12. A catheter, as claimed in claim 11, wherein said console further includes:
band pass filter means to allow transmission of selected light frequency.

13. A catheter, as claimed in claim 12, wherein said band pass filter means includes:
a first band pass filter between said light source and said light fibers to allow transmission of a selected light frequency through said catheter to cause fluorescence of cells to be treated; and
a second band pass filter between said optical assembly and said camera to allow transmissions of the fluorescence frequency only to the camera for display by said video monitor.

* * * * *